(12) United States Patent
Lee et al.

(10) Patent No.: US 12,345,707 B2
(45) Date of Patent: Jul. 1, 2025

(54) FLUORESCENCE IMAGING-BASED DEVICE FOR DETECTING MICROORGANISMS AND METHOD FOR MANUFACTURING THE SAME

(71) Applicant: RESEARCH & BUSINESS FOUNDATION SUNGKYUNKWAN UNIVERSITY, Suwon-si (KR)

(72) Inventors: Nae Eung Lee, Suwon-si (KR); Won Il Lee, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 286 days.

(21) Appl. No.: 17/120,396

(22) Filed: Dec. 14, 2020

(65) Prior Publication Data

US 2021/0181197 A1 Jun. 17, 2021

(30) Foreign Application Priority Data

Dec. 13, 2019 (KR) .................. 10-2019-0166599

(51) Int. Cl.
*G01N 33/569* (2006.01)
*B01L 3/00* (2006.01)
(Continued)

(52) U.S. Cl.
CPC .......... *G01N 33/569* (2013.01); *B01L 3/5023* (2013.01); *C12Q 1/06* (2013.01);
(Continued)

(58) Field of Classification Search
CPC ............. G01N 33/569; G01N 21/6428; G01N 33/533; G01N 33/54326;
(Continued)

(56) References Cited

U.S. PATENT DOCUMENTS

2011/0124020 A1* 5/2011 Kipps .................. G01N 33/537
435/7.92
2014/0017124 A1* 1/2014 Lee ........................ G01N 35/00
422/68.1
(Continued)

FOREIGN PATENT DOCUMENTS

KR 10-2015-0114037 A 10/2015
KR 10-2017-0022687 A 3/2017
(Continued)

OTHER PUBLICATIONS

Shrivastava, Sajal, Won-Il Lee, and Nae-Eung Lee. "Culture-free, highly sensitive, quantitative detection of bacteria from minimally processed samples using fluorescence imaging by smartphone." Biosensors and Bioelectronics 109 (2018): 90-97. (Year: 2018).*
Harpaz, Dorin, Tim Axelrod, Alicia Lu Yitian, Evgeni Eltzov, Robert S. Marks, and Alfred IY Tok. "Dissolvable polyvinyl-alcohol film, a time-barrier to modulate sample flow in a 3D-printed holder for capillary flow paper diagnostics." Materials 12, No. 3 (2019): 343. (Year: 2019).*
(Continued)

*Primary Examiner* — Elizabeth A Robinson
*Assistant Examiner* — Sophia Y Lyle
(74) *Attorney, Agent, or Firm* — NSIP Law

(57) ABSTRACT

The present invention relates to a fluorescence imaging-based device for detecting microorganisms, a manufacturing method thereof, and a method for detecting microorganisms using the same. The present invention relates to a fluorescence imaging-based device for detecting microorganisms which works with minimal user control and a method for detecting microorganisms, and enables direct observation and counting very few microorganisms within a predetermined fixed detection time.

15 Claims, 4 Drawing Sheets

(51) Int. Cl.
  *C12Q 1/06* (2006.01)
  *G01N 21/64* (2006.01)
  *G01N 33/533* (2006.01)
  *G01N 33/543* (2006.01)

(52) U.S. Cl.
  CPC ....... *G01N 21/6428* (2013.01); *G01N 33/533* (2013.01); *G01N 33/54326* (2013.01); *B01L 2300/0809* (2013.01); *G01N 2021/6439* (2013.01)

(58) Field of Classification Search
  CPC ......... G01N 2021/6439; G01N 33/582; G01N 2201/0221; G01N 21/6458; G01N 15/1484; G01N 2015/1486; B01L 3/5023; B01L 2300/0809; B01L 2200/0668; B01L 3/502761; B01L 2400/043; B01L 3/502707; B01L 3/50273; C12Q 1/06
  See application file for complete search history.

(56) References Cited

U.S. PATENT DOCUMENTS

2014/0295420 A1* 10/2014 Ovsyanko ................ B03C 1/01
   436/178
2016/0171686 A1* 6/2016 Du ..................... G01N 15/1433
   382/130

FOREIGN PATENT DOCUMENTS

| KR | 10-2047854 B1 | 12/2019 | | |
|---|---|---|---|---|
| WO | WO-2013106458 A2 | * | 7/2013 | .......... B01F 11/0071 |
| WO | WO-2019148837 A1 | * | 8/2019 | ............. G01N 21/76 |

OTHER PUBLICATIONS

Lee, Won-Il, et al. "A smartphone fluorescence imaging-based mobile biosensing system integrated with a passive fluidic control cartridge for minimal user intervention and high accuracy." Lab on a Chip 19, No. 8 (2019): 1502-1511. (Year: 2019).*

* cited by examiner

FLUORESCENCE IMAGING-BASED DEVICE FOR DETECTING MICROORGANISMS AND METHOD FOR MANUFACTURING THE SAME

CROSS-REFERENCE TO RELATED APPLICATION

This application claims priority to and the benefit of Korean Patent Application No. 10-2019-0166599, filed on Dec. 13, 2019, the disclosure of which is incorporated herein by reference in its entirety.

BACKGROUND

1. Field of the Invention

The present invention relates to a fluorescence imaging-based device for detecting microorganisms, a method for manufacturing the same, and a method for detecting microorganisms using the same.

2. Discussion of Related Art

Microorganisms harmful to humans are referred to as harmful microorganisms. These harmful microorganisms include pathogenic bacteria as well as food poisoning and high-risk infectious bacteria that cause decay and infection. Such microbial infection may lead to human and animal diseases, causing socially and economically adverse effects. Among these microorganisms, *Escherichia coli* contained in food or drinking water causes a disease such as food poisoning, resulting in serious economic losses.

For detecting pathogenic microorganisms, although a method using culture and a biochemical test is used, since it takes about 3 to 5 days, there are limitations in early detection of a pathogenic microorganism without culture. Accordingly, there is a demand for the development of technology that can quickly detect a pathogenic microorganism early, and particularly, if there is an on-site device for detecting microorganisms, which can quickly detect microorganisms in food, drinking water and industrial products, such a device will be effective in early detection of pathogenic microorganisms.

PRIOR ART DOCUMENT

Patent Document (Patent Document 1) Korean Patent No. 10-2047854

SUMMARY OF THE INVENTION

Therefore, the inventors developed a device that is able to detect a microorganism in the field, which is able to separate microorganisms present in a detection sample from other materials within a certain reaction time by the intrinsic passive mechanism of the device, and directly observe and detect the separated microorganism using a fluorescence microscope.

Therefore, the present invention is directed to providing a fluorescence imaging-based device for detecting microorganisms.

The present invention is also directed to providing a method for manufacturing a fluorescence imaging-based device for detecting microorganisms.

The present invention is also directed to providing a fluorescence imaging-based method for detecting microorganisms.

However, technical problems to be solved in the present invention are not limited to the above-described problems, and other problems which are not described herein will be fully understood by those of ordinary skill in the art from the following descriptions.

To attain the purpose of the present invention, the present invention provides a fluorescence imaging-based device for detecting microorganisms, which includes a substrate on which a magnet is disposed;

a microfluidic channel layer, which is disposed above the magnet of the substrate, has a microfluidic channel formed on a surface thereof and a separation reaction space in which a detection sample and a high-viscosity liquid are placed; and an absorption layer disposed on the microfluidic channel layer and having an empty space, wherein the empty space of the absorption layer has an area the same or smaller than that of the microfluidic channel layer such that the absorption layer and the microfluidic channel layer are in contact with each other, the detection sample is a sample containing free magnetic particles and magnetic particle-conjugated fluorescence-labeled microorganisms, when the detection sample is injected into a separation reaction space in the microfluidic channel layer, the free magnetic particles in the detection sample reach the absorption layer through a microfluidic channel formed in the microfluidic channel layer along with the high-viscosity liquid, and then are absorbed to be removed, and the magnetic particle-conjugated fluorescence-labeled microorganisms in the detection sample are captured by the magnet in the separation reaction space.

In addition, the present invention provides a method for manufacturing a fluorescence imaging-based device for detecting microorganisms, which includes the following steps:

(a) preparing a microfluidic channel layer by forming a separation reaction space in which a detection sample and a high-viscosity liquid are to be placed in a material for a microfluidic channel layer, and forming a microfluidic channel on its surface;

(b) attaching the microfluidic channel layer to the top of a substrate with a magnet;

(c) preparing an absorption layer by forming an empty space in a material for an absorption layer, in which the empty space of the absorption layer has an area the same or smaller than that of the microfluidic channel layer such that the absorption layer is in contact with the microfluidic channel layer; and (d) placing the absorption layer on the microfluidic channel layer attached to the substrate.

In addition, the present invention provides a fluorescence imaging-based method for detecting microorganisms, which includes the following steps:

injecting a high-viscosity liquid and a detection sample into the fluorescence imaging-based device for detecting microorganisms to separate magnetic particle-conjugated fluorescence-labeled microorganisms from free magnetic particles in the detection sample; and after the completion of the separation, observing the magnetic particle-conjugated fluorescence-labeled microorganisms captured by a magnet in a separation reaction space using a fluorescence microscope.

In one embodiment of the present invention, the separation reaction space is an empty space formed in the microfluidic channel layer, and may have a magnet under the empty space.

In another embodiment of the present invention, due to an area difference between the separation reaction space formed in the microfluidic channel layer and the empty space formed in the absorption layer, a separation reaction time for separating the magnetic particle-conjugated fluorescence-labeled microorganisms from the free magnetic particles in the detection sample may be adjusted.

In still another embodiment of the present invention, the microfluidic channel layer may be a water-soluble polymer.

In yet another embodiment of the present invention, the water-soluble polymer may be selected from the group consisting of polyethylene glycol, polyvinylpyrrolidone, polyvinyl alcohol, polyacrylic acid, polyacrylamide, carboxymethyl cellulose, pullulan and hydroxypropyl cellulose.

In yet another embodiment of the present invention, the high-viscosity liquid may be a liquid material having a viscosity of 20 to 200 mPa·s at room temperature.

In yet another embodiment of the present invention, the high-viscosity liquid may be selected from the group consisting of glycerol, polyethylene glycol, polyvinylpyrrolidone and an aqueous solution thereof.

In yet another embodiment of the present invention, the magnetic particle-conjugated fluorescence-labeled microorganisms captured by the magnet may be observed or counted using a fluorescence microscope.

In yet another embodiment of the present invention, the microorganism detection device may further include an upper case disposed on the absorption layer and having a columnar injection channel connected to the separation reaction space; and a lower case disposed under the substrate and connected with the upper case.

In yet another embodiment of the present invention, the microorganism detection device may be portable.

In yet another embodiment of the present invention, Step (a) may be for forming a microfluidic channel by humidifying a material for the microfluidic channel layer to disintegrate surface texture and then drying the material.

In yet another embodiment of the present invention, Step (a) may be for forming a microfluidic channel by micropattern stamping the material for the microfluidic channel layer.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
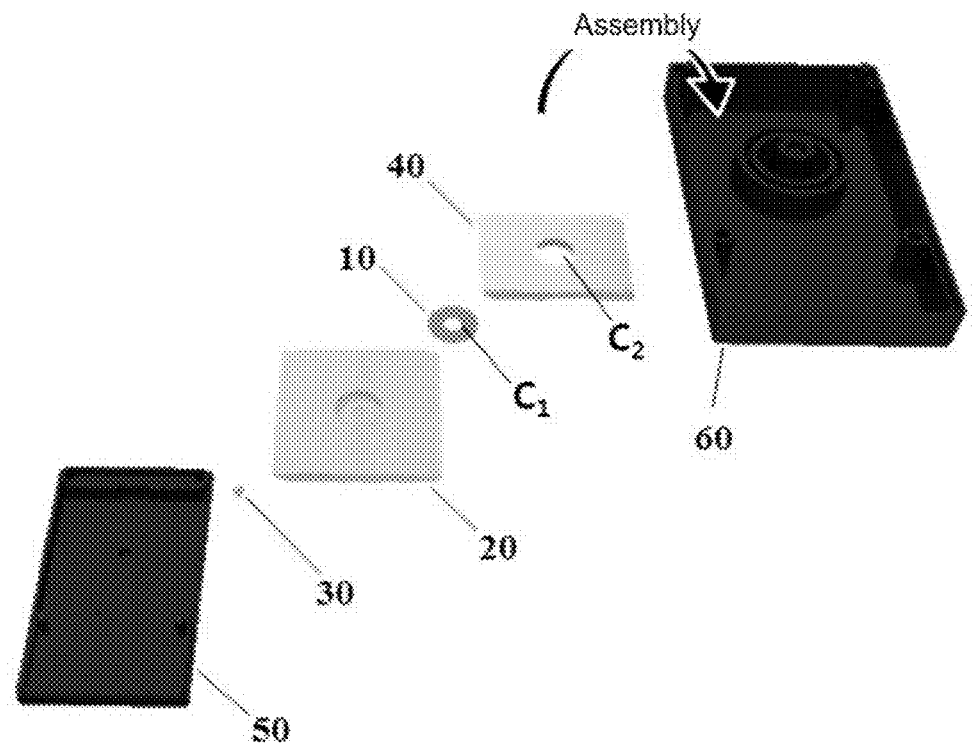
FIG. 1 is a schematic diagram of a fluorescence imaging-based device for detecting microorganisms according to one embodiment of the present invention.

Hereinafter, embodiments of the present invention will be described in further detail with reference to the accompanying drawings. The embodiments of the present invention may be modified in a variety of different forms, and it should not be construed that the scope of the present invention is not limited to the following embodiments. The embodiments of the present invention are provided to more completely explain the present invention to those of ordinary skill in the art. Therefore, the shape of the elements in the drawings may be exaggerated to emphasize clearer explanation. In addition, terms and words used in the specification and claims should not be construed as limited to general or dictionary terms meanings, and should be interpreted with the meaning and concept in accordance with the technical idea of the present invention based on the principle that the inventors have appropriately defined the concepts of terms in order to explain the invention in the best way.

When describing with reference to the drawings, the same or corresponding components are denoted by the like reference numerals, and duplicated descriptions thereof will be omitted.

FIG. 1 is a schematic diagram of a fluorescence imaging-based device for detecting microorganisms according to one embodiment of the present invention.

Referring to FIG. 1, the fluorescence imaging-based device for detecting microorganisms according to one embodiment of the present invention includes a substrate 20 on which a magnet 30 is disposed, a microfluidic channel layer 10, which is disposed on the magnet 30 of the substrate 20 and has a microfluidic channel on the surface thereof and a separation reaction space $C_1$ in which a detection sample and a high-viscosity liquid are placed, and an absorption layer 40 disposed on the microfluidic channel layer 10 and provided with an empty space $C_2$ therein.

The magnet 30 is disposed on the substrate 20, and serves to capture magnetic particle-conjugated fluorescence-labeled microorganisms to be detected in the separation reaction space $C_1$ formed in the microfluidic channel layer 10. As the substrate 20, a polycarbonate-based, acryl-based or polyethylene-based plastic may be used. The shape of the magnet 30 is not particularly limited, and may be, for example, a round magnet.

The microfluidic channel layer 10 is disposed on the magnet 30 disposed on the substrate 20, and has a microfluidic channel through which a high-viscosity liquid can flow on the surface. In addition, the detection sample and the high-viscosity liquid are placed in the microfluidic channel layer 10, and as described below, there is the separation reaction space $C_1$ in which free magnetic particles and magnetic particle-conjugated fluorescence-labeled microorganisms present in the detection sample are separated. When a user injects the high-viscosity liquid and then the detection sample into the microorganism detection device of the present invention, the high-viscosity liquid and detection sample injected herein are placed in the separation reaction space $C_1$, and the injected high-viscosity liquid flows through the microfluidic channel formed on the surface of the microfluidic channel layer 10 toward the absorption layer 40.

The separation reaction space $C_1$ may be an empty space formed in the microfluidic channel layer 10, and the magnet 30 for capturing magnetic particle-conjugated fluorescence-labeled microorganisms in the detection sample may be disposed under the empty space. The empty space may be formed by cutting out the inside of a material for the microfluidic channel layer (e.g., a double-sided tape formed of a water-soluble polymer) in a round shape.

The microfluidic channel layer 10 may be formed of a water-soluble polymer, and examples of the water-soluble polymer usable for the present invention may include, for example, polyethylene glycol, polyvinylpyrrolidone, polyvinyl alcohol, polyacrylic acid, polyacrylamide, carboxymethyl cellulose, pullulan or hydroxypropyl cellulose.

The absorption layer 40 is placed on the microfluidic channel layer 10, and has an empty space $C_2$ therein. The high-viscosity liquid and detection sample injected into the microorganism detection device of the present invention are placed in the separation reaction space $C_1$ formed in the microfluidic channel layer 10 through the empty space $C_2$ formed in the absorption layer 40.

In the microorganism detection device of the present invention, a separation reaction time for separating microorganism-bound magnetic particles (magnetic particle-conjugated fluorescence-labeled microorganisms) from the free magnetic particles (magnetic particles not conjugated to microorganisms) in the detection sample may be adjusted by an area difference between the separation reaction space $C_1$ formed in the microfluidic channel layer 10 and the empty space $C_2$ formed in the absorption layer 40. To adjust the separation reaction time, the empty space $C_2$ of the absorption layer 40 has an area that is the same or smaller than the microfluidic channel layer 10 such that the absorption layer 40 may be in contact with the microfluidic channel layer 10. If the empty space $C_2$ of the absorption layer 40 is larger than the area of the microfluidic channel layer 10, the high-viscosity liquid and the detection sample flowing through the microfluidic channel of the microfluidic channel layer 10 may be absorbed into the absorption layer 40.

The detection sample may be a liquid sample which is expected to have microorganisms to be detected. The detection sample may be prepared by adding fluorescence-labeled magnetic particles (e.g., nano-sized magnetic particles) to a sample to be detected, and therefore, the free magnetic particles (and other impurities) not bound to the microorganism and magnetic particles bound to the microorganism (fluorescence-labeled) are mixed in the detection sample.

As shown in FIG. 1, the fluorescence imaging-based device for detecting microorganisms according to one embodiment of the present invention may further include an upper case 60 and a lower case 50.

The upper case 60 is disposed on the absorption layer 40, and includes a columnar injection channel connected to the separation reaction space $C_1$ formed in the microfluidic channel layer 10. The high-viscosity liquid and the detection sample are injected into the separation reaction space $C_1$ of the microfluidic channel layer 10 through the injection channel.

The lower case 50 may be disposed under the substrate 20 and connected with the upper case 60, and the substrate 20, the microfluidic channel layer 10 and the absorption layer 40 are placed in the upper and lower cases 50 and 60.

Figure 2:
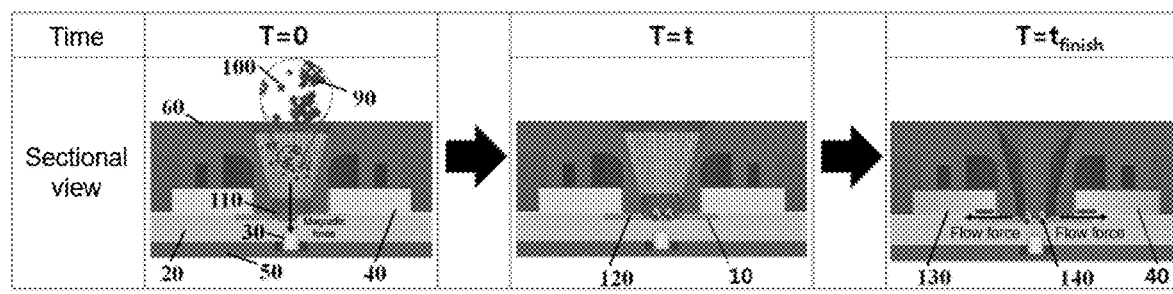
FIG. 2 is a diagram illustrating operational changes over time after a detection sample is injected into a fluorescence imaging-based device for detecting microorganisms according to one embodiment of the present invention.

FIG. 2 is a diagram illustrating operational changes over time after a detection sample is injected into a fluorescence imaging-based device for detecting microorganisms according to one embodiment of the present invention.

Referring to FIG. 2, the operation of the present invention will be described in detail.

When the high-viscosity liquid 110 and then the detection sample (magnetic particle-conjugated fluorescence-labeled microorganisms 90 and free magnetic particles 100) are injected into the fluorescence imaging-based device for detecting microorganisms according to one embodiment of the present invention, separation between the magnetic particle-conjugated fluorescence-labeled microorganisms and the free magnetic particles occurs due to a magnetic force from time t to time $t_{finish}$ as the high-viscosity liquid flows through a microfluidic channel on the surface of the microfluidic channel layer 10 due to a capillary phenomenon (120). At the time $t_{finish}$, due to a flow force caused by the absorption force of the absorption layer 40, passive absorption of the free magnetic particles and the detection sample solution occurs (130), and the magnetic particle-conjugated fluorescence-labeled microorganisms are influenced by a stronger magnetic force, followed by separation and capture onto a capturing surface (140) (the separation reaction space of the microfluidic channel layer). The magnetic particle-conjugated fluorescence-labeled microorganisms captured by the magnet may be observed or counted using a fluorescence microscope.

Figure 3:
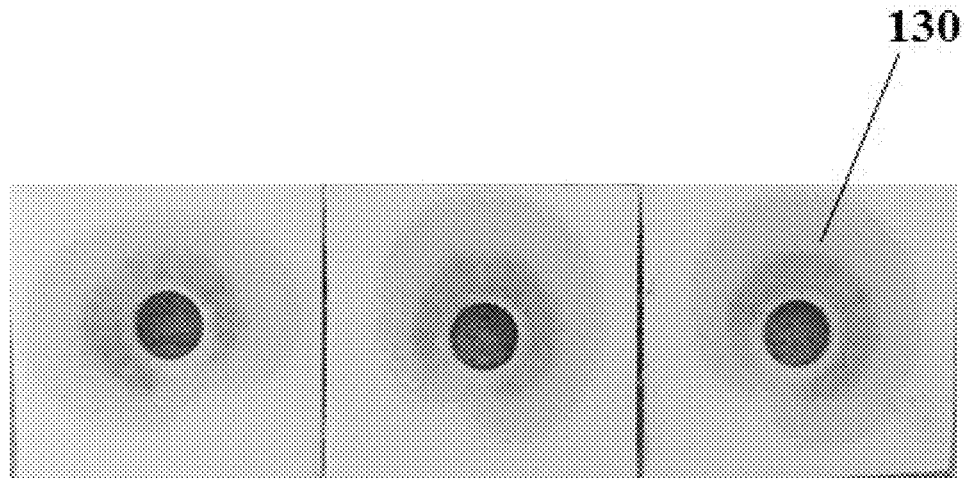
FIG. 3 is a photograph showing that a high-viscosity liquid (glycerol) dyed green and free magnetic particles are actually absorbed in an absorption layer, which results from operation of three fluorescence imaging-based devices for detecting microorganisms according to one embodiment of the present invention.

FIG. 3 is a photograph showing that a high-viscosity liquid (glycerol) dyed green and free magnetic particles are actually absorbed in an absorption layer, which results from the operation of three fluorescence imaging-based devices for detecting microorganisms according to one embodiment of the present invention.

The high-viscosity liquid flows through the microfluidic channel of the microfluidic channel layer 10 toward the absorption layer 40, resulting in absorption into the absorption layer 40. As the high-viscosity liquid of the present invention, for example, a liquid material having a viscosity of 20 to 200 mPa·s may be used. In another example, as the high-viscosity liquid, a solution selected from the group consisting of glycerol, polyethylene glycol, polyvinylpyrrolidone and an aqueous solution thereof may be used.

Hereinafter, a method for manufacturing a fluorescence imaging-based device for detecting microorganisms according to one embodiment of the present invention will be described, and duplicated description of the same parts of the above-described fluorescence imaging-based device for detecting microorganisms will be omitted.

Figure 4:
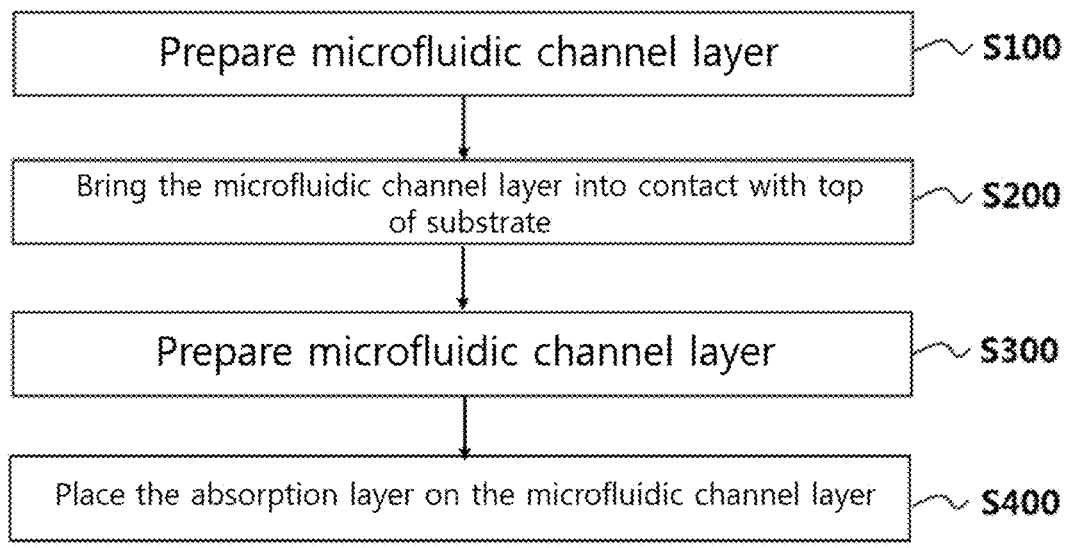
FIG. 4 is a flow chart showing a method for manufacturing a fluorescence imaging-based device for detecting microorganisms according to one embodiment of the present invention.
Figure 5:
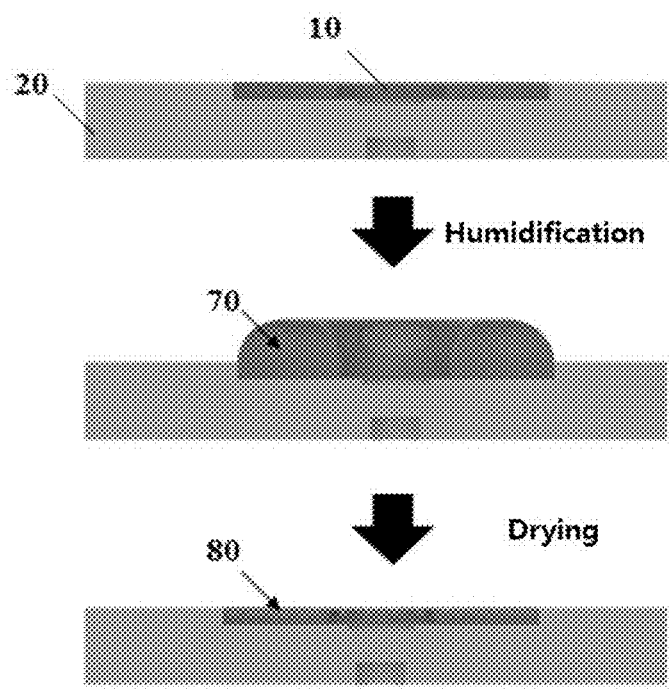
FIG. 5 is a diagram showing one example of forming a microfluidic channel on the surface of a microfluidic channel layer.

FIG. 4 is a flow chart showing a method for manufacturing a fluorescence imaging-based device for detecting microorganisms according to one embodiment of the present invention, and FIG. 5 is a diagram showing one example of forming a microfluidic channel on the surface of a microfluidic channel layer.

Referring to FIG. 4, the method for manufacturing a fluorescence imaging-based device for detecting microorganisms according to one embodiment of the present invention includes preparing a microfluidic channel layer by forming a separation reaction space in which a detection sample and a high-viscosity liquid are to be placed in a material for a microfluidic channel layer, and forming a microfluidic channel on its surface (S100), attaching the microfluidic channel layer to the top of a substrate with a magnet (S200), preparing an absorption layer by forming an empty space in a material for an absorption layer (S300), and placing the absorption layer on the microfluidic channel layer attached to the substrate (S400).

In S100, a microfluidic channel layer 10 having a separation reaction space $C_1$ is prepared. As a material for the microfluidic channel layer, a water-soluble polymer may be used, and to reinforce portability, a thin, round or polygonal water-soluble double-sided tape (e.g., diameter: 1 to 2 cm) may be used.

The separation reaction space $C_1$ may be formed by cutting the center of the microfluidic channel layer into a round or polygonal shape. The size of the separation reaction space $C_1$ can be freely changed according to an amount of the detection sample or the separation reaction time of a target detection sample detection sample (time for separating the magnetic particle-conjugated fluorescence-labeled microorganisms from the free magnetic particles in the detection sample).

To form a microfluidic channel, a method for forming a microfluidic channel, which is known in the art, may be used without limitation. For example, as shown in FIG. 5, surface texture 70 may be disintegrated by humidifying the material for the microfluidic channel layer and then dried, thereby forming a microfluidic channel 80. In another example, a microfluidic channel may be formed by micro-pattern stamping.

In S200, the prepared microfluidic channel layer 10 is adhered to the upper surface of a substrate 20 on which a magnet 30 is disposed.

In S300, an absorption layer 40 is prepared by forming an empty space $C_2$ in the material for an absorption layer. As the material for the absorption layer, an absorption pad may be used, and for example, a square pad having a thickness of 2 mm or less and a length of 2 to 3 cm may be used. The shape and type of the absorption layer 40 may vary according to a detection sample or other conditions. As the material for the absorption layer, a porous membrane such as paper, cotton or fabric may be used.

The empty space $C_2$ in the absorption layer 40 may be formed by cutting the center of the absorption layer 40 into a round or polygonal shape, like the separation reaction space $C_1$ of the microfluidic channel layer 10. As described above, by using the difference in size between the empty space $C_2$ and the separation reaction space $C_1$ (the cut empty space) formed in the microfluidic channel layer 10, the reaction time for separating the detection sample may be adjusted.

In S400, the absorption layer 40 is placed on the microfluidic channel layer 10 adhered to the substrate 20. In addition, a microorganism detection device may be manufactured by additionally connecting upper and lower cases 50 and 60 to a combination of the substrate 20, the microfluidic channel layer 10 and the absorption layer 40.

The above-described microorganism detection device of the present invention has the following features.

Figure 6:
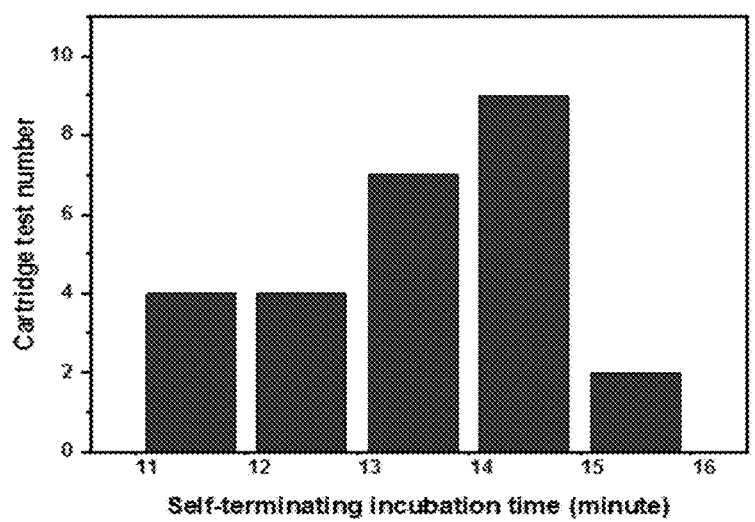
FIG. 6 is a diagram showing that a separation reaction is completed in approximately 15 minutes as a result of testing a total of 26 cartridge-type microorganism detection devices, as an example for verifying the application of a fluorescence imaging-based device for detecting microorganisms according to one embodiment of the present invention.

In the manufacturing process, the microorganism detection device of the present invention may adjust a separation reaction time by adjusting the size (e.g., diameter) difference between $C_1$ and $C_2$, and fix a certain time. FIG. 6 is a diagram showing that the separation reaction is completed in approximately 15 minutes as a result of testing a total of 26 cartridge-type microorganism detection devices, as an example for verifying the application of a microorganism detection device of the present invention.

In addition, since free magnetic particles and the entire liquid sample are removed due to a flow force caused by the absorption force of the absorption layer after the end of the reaction time for passive separation of magnetic particle-conjugated fluorescence-labeled microorganisms, sample microorganisms can be directly observed and counted by fluorescence microscope microimaging without additional and complicated manipulation for detection, resulting in enhancement of ease of use.

In addition, by making the area of a capturing surface where the magnetic particle-conjugated fluorescence-labeled microorganisms completely separated from the free magnetic particles are captured smaller than the area of the field of view of the fluorescence microimaging, the captured fluorescence-labeled microorganisms may be directly observed, and even a very small number of microorganisms can be accurately detected by counting.

Hereinafter, to help in understanding the present invention, exemplary examples will be suggested. However, the following examples are merely provided to more easily understand the present invention, and not to limit the present invention.

EXAMPLES

Example 1. Manufacture of Fluorescence Imaging-Based Device for Detecting Microorganisms The center of a double-sided tape based on a water-soluble polymer (polyvinyl alcohol) having a diameter of 0.8 cm serving as a microfluidic channel layer was cut into a round shape ($C_1$), and the cut water-soluble double-sided tape was aligned and adhered to the center of a capturing surface of a transparent plastic substrate (polycarbonate) into which a round magnet (neodymium) was inserted. To cause the capillary phenomenon of a high-viscosity liquid to the surface of the microfluidic channel layer, the texture was disintegrated by humidifying the water-soluble double-sided tape and then dried for recombination, thereby forming a microfluidic channel on the surface (FIG. 5).

The center of a square absorption pad having an area of 1 cm² was cut into a round shape ($C_2$), and aligned on the water-soluble double-sided tape to be concentric with $C_1$ ($C_1$ diameter<$C_2$ diameter, separation reaction time can be adjusted by a change of the difference in diameter between two circles). After alignment, a cup-shaped injection channel, which can contain a certain volume of liquid detection sample, was placed between the upper case and the lower case, and both cases were assembled, thereby manufacturing a cartridge-type microorganism detection device.

Example 2. Observation and Counting of Microorganisms using Fluorescence Imaging-Based Device for Detecting Microorganisms A mixed sample of free magnetic particles and magnetic particle-conjugated fluorescence-labeled microorganisms was prepared by a method for first reacting capture particle-coated magnetic particles with microorganisms and staining the microorganisms by adding fluorescent particles to the reaction product. A high-viscosity liquid (glycerol having a viscosity of 20 mPa·s or more at room temperature) was pre-injected into a cup-shaped injection channel that can hold a liquid detection sample of the microorganism detection device, followed by injection of a detection sample in which free magnetic particles and magnetic particle-conjugated fluorescence-labeled microorganisms are mixed. When the high-viscosity liquid flowed through a microfluidic channel on the surface of the microfluidic channel layer due to the capillary phenomenon while the flow of the detection sample stopped, and came into contact with the outer absorption pad, the entire liquid sample was passively and instantly absorbed into an absorption pad while leaving the magnetic particle-conjugated fluorescence-labeled microorganisms on the opposite side of the region of a transparent substrate on which a magnet was placed (on the magnet), and the separation reaction time ended. During the passively controlled separation reaction time, the magnetic particle-conjugated fluorescence-labeled microorganisms in the high-viscosity liquid were separated from free magnetic particles and captured on the substrate surface due to the influence induced by larger magnetic force generated by the magnet inserted into the substrate, and after the completion of the reaction, free magnetic particles remaining in the high-viscosity liquid were removed with the entire liquid sample by flow force formed by the absorption force of the absorption pad.

Figure 7:
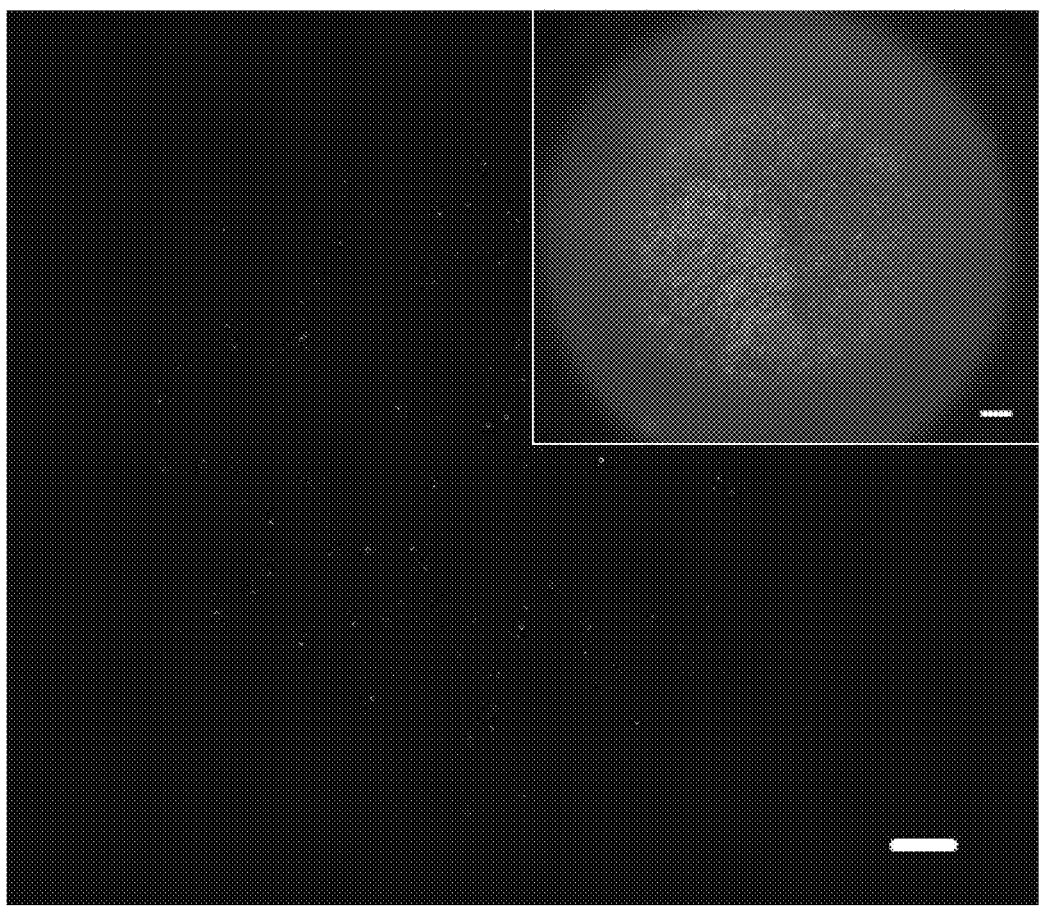
FIG. 7 shows the result of counting magnetic particle-conjugated fluorescence-labeled *Staphylococcus aureus* of 100 CFU or less within 100 μL, which was captured on the capturing surface of a substrate through fluorescence microimaging, after a cartridge-type fluorescence imaging-based device for detecting microorganisms according to one embodiment of the present invention is operated.

The area of the surface where the fluorescence-labeled microorganisms are captured by the magnet was designed to be smaller than that of the field of view of the microscopic magnification capable of individually identifying microorganisms (10× or greater objective lens), and thus all microorganisms captured thereon were able to be observed or counted (FIG. 7). FIG. 7 shows the result of counting magnetic particle-conjugated fluorescence-labeled *Staphylococcus aureus* of 100 CFU or less within 100 μL, which was captured on the capturing surface of a substrate through fluorescence microimaging, after operating a cartridge-type fluorescence imaging-based device for detecting microorganisms.

The present invention relates to a fluorescence imaging-based device for detecting microorganisms which works with minimal user control and a method for detecting microorganisms, and enables direct observation and counting of a very few microorganisms within a predetermined fixed detection time. In addition, the microorganism detection device of the present invention can be manufactured in the form of a small cartridge, and thus can be used as an on-site device for detecting microorganisms.

It should be understood by those of ordinary skill in the art that the above descriptions of the present invention are exemplary, and the embodiments disclosed herein can be easily modified into other specific forms without changing the technical spirit or essential features of the present invention. Therefore, it should be interpreted that the embodiments described above are exemplary in all aspects, and are not limitative.

What is claimed is:

1. A fluorescence imaging-based device for detecting microorganisms, comprising:
   a magnet;
   a substrate on which the magnet is disposed;
   a microfluidic channel layer, which is disposed in an annular configuration above the magnet, having a microfluidic channel formed on a surface thereof and having a separation reaction space configured to hold a detection sample and a high-viscosity liquid at a radial center of the annular configuration; and
   an absorption layer disposed on the microfluidic channel layer and having an empty space penetrating the absorption layer,
   wherein, in a plan view, an area of the empty space penetrating the absorption layer is greater than an area of the separation reaction space and the same or smaller than an area of the microfluidic channel layer, and the absorption layer and the microfluidic channel layer are in direct contact with each other,
   when the detection sample is injected into the separation reaction space in the microfluidic channel layer, and the detection sample comprises free magnetic particles and magnetic particle-conjugated fluorescence-labeled microorganisms,
   the microfluidic channel layer is configured so that the free magnetic particles in the detection sample reach the absorption layer through the microfluidic channel formed in the microfluidic channel layer along with the high-viscosity liquid, and then are absorbed by the absorption layer to be removed from the separation reaction space, and
   the magnetic particle-conjugated fluorescence-labeled microorganisms in the detection sample are captured by the magnet in the separation reaction space.

2. The device of claim 1, wherein the separation reaction space is an empty space in the microfluidic channel layer, and there is the magnet under the empty space.

3. The device of claim 1, wherein the separation reaction space communicates with the empty space of the absorption layer; and
   a separation reaction time for separating the magnetic particle-conjugated fluorescence-labeled microorganisms from the free magnetic particles in the detection sample depends on an area difference between the separation reaction space formed in the microfluidic channel layer and the empty space formed in the absorption layer.

4. The device of claim 1, wherein the microfluidic channel layer is a water-soluble polymer.

5. The device of claim 4, wherein the water-soluble polymer is selected from the group consisting of polyethylene glycol, polyvinylpyrrolidone, polyvinyl alcohol, polyacrylic acid, polyacrylamide, carboxymethyl cellulose, pullulan and hydroxypropyl cellulose.

6. The device of claim 4, wherein the water-soluble polymer is in the shape of a tape having a diameter of 1 to 2 cm.

7. The device of claim 1, wherein the high-viscosity liquid has a viscosity of 20 to 200 mPa·s at room temperature.

8. The device of claim 1, wherein the high-viscosity liquid comprises at least one solution selected from the group consisting of glycerol, polyethylene glycol, polyvinylpyrrolidone, an aqueous solution of glycerol, an aqueous solution of polyethylene glycol, an aqueous solution of polyvinylpyrrolidone, and a combination thereof.

9. The device of claim 1, wherein the magnetic particle-conjugated fluorescence-labeled microorganisms captured by the magnet are observed or counted using a fluorescence microscope.

10. The device of claim 1, further comprising:
    an upper case disposed on the absorption layer and having a columnar injection channel inserted through the empty space penetrating the absorption layer and connected to the separation reaction space; and a lower case disposed under the substrate and connected with the upper case.

11. The device of claim 1, wherein the device for detecting microorganisms is portable.

12. The device of claim 1, wherein the magnet is configured to exert a magnetic force on the magnetic particle-conjugated fluorescence-labeled microorganisms that is stronger than a flow force on the magnetic particle-conjugated fluorescence-labeled microorganisms exerted by the high-viscosity liquid flowing to the absorption layer, and
wherein the magnet is configured to exert a magnetic force on the free magnetic particles that is weaker than a flow force on the free magnetic particles exerted by the high-viscosity liquid flowing to the absorption layer.

13. A system for detecting microorganisms, comprising:
the fluorescence imaging-based device according to claim 1 wherein the microfluidic channel formed on the surface of the microfluidic channel layer is configured to direct flow of the high-viscosity liquid by capillary effect, and
a sample preparation mixture comprising the high-viscosity liquid and fluorescence-labeled magnetic particles;
wherein, when the microorganisms to be detected are combined with the sample preparation mixture to thereby form a mixed sample,
(i) the fluorescence-labeled magnetic particles that bind to the microorganisms to be detected form, together with the microorganisms to be detected, the magnetic particle-conjugated fluorescence-labeled microorganisms, and
(ii) the fluorescence-labeled magnetic particles that do not bind to the microorganisms to be detected are the free magnetic particles;
wherein, when the mixed sample is injected into the separation reaction space in the microfluidic channel layer,
(i) the flow of the high-viscosity liquid directed through the microfluidic channel by capillary effect removes the free magnetic particles away from the separation reaction space and toward the absorption layer, and
(ii) the magnetic particle-conjugated fluorescence-labeled microorganisms are captured by the magnet in the separation reaction space;
wherein the magnet is configured to exert a magnetic force on the magnetic particle-conjugated fluorescence-labeled microorganisms that is stronger than a flow force on the magnetic particle-conjugated fluorescence-labeled microorganisms exerted by the high-viscosity liquid flowing toward the absorption layer; and
wherein the magnet is configured to exert a magnetic force on the free magnetic particles that is weaker than a flow force on the free magnetic particles exerted by the high-viscosity liquid flowing toward the absorption layer.

14. A fluorescence imaging-based device for detecting microorganisms, comprising:
a microfluidic channel layer having an annular configuration and comprising a microfluidic channel formed on a surface of the microfluidic channel layer and a separation reaction space formed at a radial center of the annular configuration in communication with the microfluidic channel;
a magnet disposed in a vicinity of the separation reaction space and configured to attract magnetic particle-conjugated fluorescence-labeled microorganisms introduced to the separation reaction space when a detection sample comprising free magnetic particles and the magnetic particle-conjugated fluorescence-labeled microorganisms is introduced into the separation reaction space with a high-viscosity liquid; and
an absorption layer disposed on the microfluidic channel layer, the absorption layer having an opening formed therein to allow the detection sample to be placed directly on the separation reaction space, a surface of the absorption layer formed over the microfluidic channel such that the high-viscosity liquid moves along the microfluidic channel and is absorbed by the absorption layer in response to the high-viscosity liquid being placed in the separation reaction space, while the magnet is configured to hold the magnetic particle-conjugated fluorescence-labeled microorganisms in the separation reaction space for an imaging-based detection of the microorganisms,
wherein the microfluidic channel formed on the surface of the microfluidic channel layer is configured to direct flow of the high-viscosity liquid by capillary effect.

15. The device of claim 14, wherein the microfluidic channel layer is configured to allow the detection sample and the high-viscosity liquid placed directly on the separation reaction space to move peripherally along the microfluidic channel and be absorbed by the absorption layer to be separated from the magnetic particle-conjugated fluorescence-labeled microorganisms that are held in place on the separation reaction space by the magnet.

* * * * *